United States Patent [19]

Kato

[11] Patent Number: 5,029,589

[45] Date of Patent: Jul. 9, 1991

[54] APPARATUS FOR AUTOMATICALLY MEASURING BLOOD PRESSURE

[75] Inventor: Yoichi Kato, Nara, Japan

[73] Assignee: Sharp Kabushiki Kaisha, Osaka, Japan

[21] Appl. No.: 375,406

[22] Filed: Jul. 3, 1989

[30] Foreign Application Priority Data

Jul. 1, 1988 [JP] Japan ............................. 63-88412[U]

[51] Int. Cl.$^5$ .............................................. A61B 5/02
[52] U.S. Cl. .................................... 128/682; 128/677
[58] Field of Search ......................... 128/672, 677–686

[56] References Cited

U.S. PATENT DOCUMENTS 4,461,266  1/1984  Hood, Jr. et al.
4,546,775  10/1985  Medero ................................ 128/681
4,660,567  4/1987  Kaneko et al. ...................... 128/680

Primary Examiner—Max Hindenburg
Assistant Examiner—Robin R. Longo
Attorney, Agent, or Firm—Irell & Manella

[57] ABSTRACT

In a hematomanometer in which the blood pressure values are detected while increasing the cuff pressure, the cuff pressure is increased to a predetermined value, the minimum blood pressure is presumed. When the presumed value is greater than a first reference value which is larger than the predetermined value, the measurement of the blood pressure is conducted while increasing the cuff pressure. When the presumed value is greater than the first reference value, the cuff pressure is decreased to a second reference value which is smaller than the predetermined value, and then the measurement of the blood pressure is conducted while increasing the cuff pressure.

2 Claims, 7 Drawing Sheets

APPARATUS FOR AUTOMATICALLY MEASURING BLOOD PRESSURE

BACKGROUND OF THE INVENTION

1. Field of the Invention

This invention relates to an apparatus for automatically measuring blood pressure such as so-called electronic hematomanometer in which blood pressure is measured by the oscillometric method.

2. Description of the Prior Art

In the oscillometric method, blood pressure is measured on the basis of minute pressure pulses (pulse wave) which are transmitted to a cuff in accompanying with fluctuation of blood pressure of a body to be measured. A conventional hematomanometer employing this oscillometric method measures the maximum and minimum blood pressures as follows: At first, the pressure of a cuff is raised at a single stroke to a high pressure level which exceeds the maximum blood pressure of a subject. Thereafter, the air in the cuff is gradually discharged to reduce the pressure of the cuff. On the way of this discharge, the pulse wave is detected by a pulse pressure sensor to determine the maximum and minimum blood pressure values.

Another hematomanometer which is of a so-called pressure-raising type measures the maximum and minimum blood pressures while increasing the pressure of a cuff. An improved hematomanometer of the pressure-raising type has been proposed in U.S. patent application Ser. No. 199,098 filed May 26, 1988. In the hematomanometer, the pressure of a cuff is raised intermittently as shown in FIG. 9, and the pulse wave is detected at the stopping periods during when the increase of the pressure is halted (i.e., at the pressures $P_1$, $P_2$, $P_3$, . . . ), and the maximum and minimum blood pressure values are determined on the basis of the detected amplitudes of the pulse wave. The U.S. Pat. No. 4,461,266 discloses a hematomanometer employing a detection principle which is similar to that described above.

A hematomanometer of the pressure-raising type has various advantages. For example, as the maximum and minimum blood pressure values are measured while increasing the pressure of a cuff, the time required for compressing the arm of a subject by a cuff of a high pressure can be reduced, thereby eliminating an unnecessary sense of tight binding and pain caused thereby. It is not necessary to set the pressure of a cuff to be raised, in advance of the measurement of blood pressure, resulting in making the hematomanometers easy to operate. As amplitudes of the pulse waves are detected while the pressure-raising operation is halted, moreover, the detected signals are not affected by noises, so that the minimum blood pressure value can be accurately detected even when the minimum blood pressure is low (i.e., the amplitudes of the pulse wave in the vicinity of the minimum blood pressure are low).

However, such a hematomanometer of the pressure-raising type has a disadvantage in that it requires a long period of time for determining the maximum and minimum blood pressure values because the pressure of a cuff is escalated step by step from a zero level.

SUMMARY OF THE INVENTION

The apparatus for automatically measuring blood pressure of this invention, which overcomes the above-discussed and numerous other disadvantages and deficiencies of the prior art, comprises a cuff; a pressure means for applying a pressure to said cuff; a first pressure control means for controlling said pressure means to increase intermittently the pressure of said cuff; a detector for detecting pressure pulses generated in said cuff; a pressure reducing means for reducing the pressure of said cuff; and a blood pressure measuring means for obtaining the minimum and maximum blood pressure values from pressure pulses which are detected during the stopping periods of the pressure increase, the improvement exists in that said apparatus further comprises; a second pressure control means for controlling said pressure means to increase continuously the pressure of said cuff to a predetermined value; a pressure presumption means for presuming the value of the minimum blood pressure from the amplitudes of pressure pulses detected by said detector after the completion of the continuous pressure increase; a comparison means for comparing said presumption value with a first reference value which is greater than said predetermined value, said comparison means producing a signal to commence the operation of said first pressure control means when said presumed value is greater than said first reference value; and a third pressure control means for controlling said pressure reducing means to reduce the pressure of said cuff to a second reference value which is smaller than said first reference value, said third pressure control means producing a signal to commence the operation of said pressure control means when the pressure of said cuff has been reduced to said second reference value.

The apparatus of the invention as set forth in the above is diagrammatically illustrated in FIG. 1.

In a preferred embodiment, the apparatus further comprises a further comparison means for comparing said presumed value with a third reference value which is between said first reference value and said second reference value, and a fourth pressure control means for controlling said pressure reducing means to reduce the pressure of said cuff to a fourth reference value which is smaller than said second reference value, said further comparison means producing a signal to commence the operation of said third pressure control means when said presumed value is greater than said third reference value, and said further comparison means producing a signal to commence the operation of said fourth pressure control means when said presumed value is smaller than said third reference value.

Thus, the invention described herein makes possible the objectives of: (1) providing an apparatus for automatically measuring blood pressure by which blood pressure values can be obtained in a short period of time; (2) providing an apparatus for automatically measuring blood pressure which requires a reduced period of time of applying a high pressure to a subject; (3) providing an apparatus for automatically measuring blood pressure which is easy to operate; and (4) providing an apparatus for automatically measuring blood pressure which can detect accurately the minimum blood pressure even when the minimum blood pressure of a subject is low.

BRIEF DESCRIPTION OF THE DRAWINGS

This invention may be better understood and its numerous objects and advantages will become apparent to those skilled in the art by reference to the accompanying drawings as follows.

DESCRIPTION OF THE PREFERRED EMBODIMENTS

Figure 1:
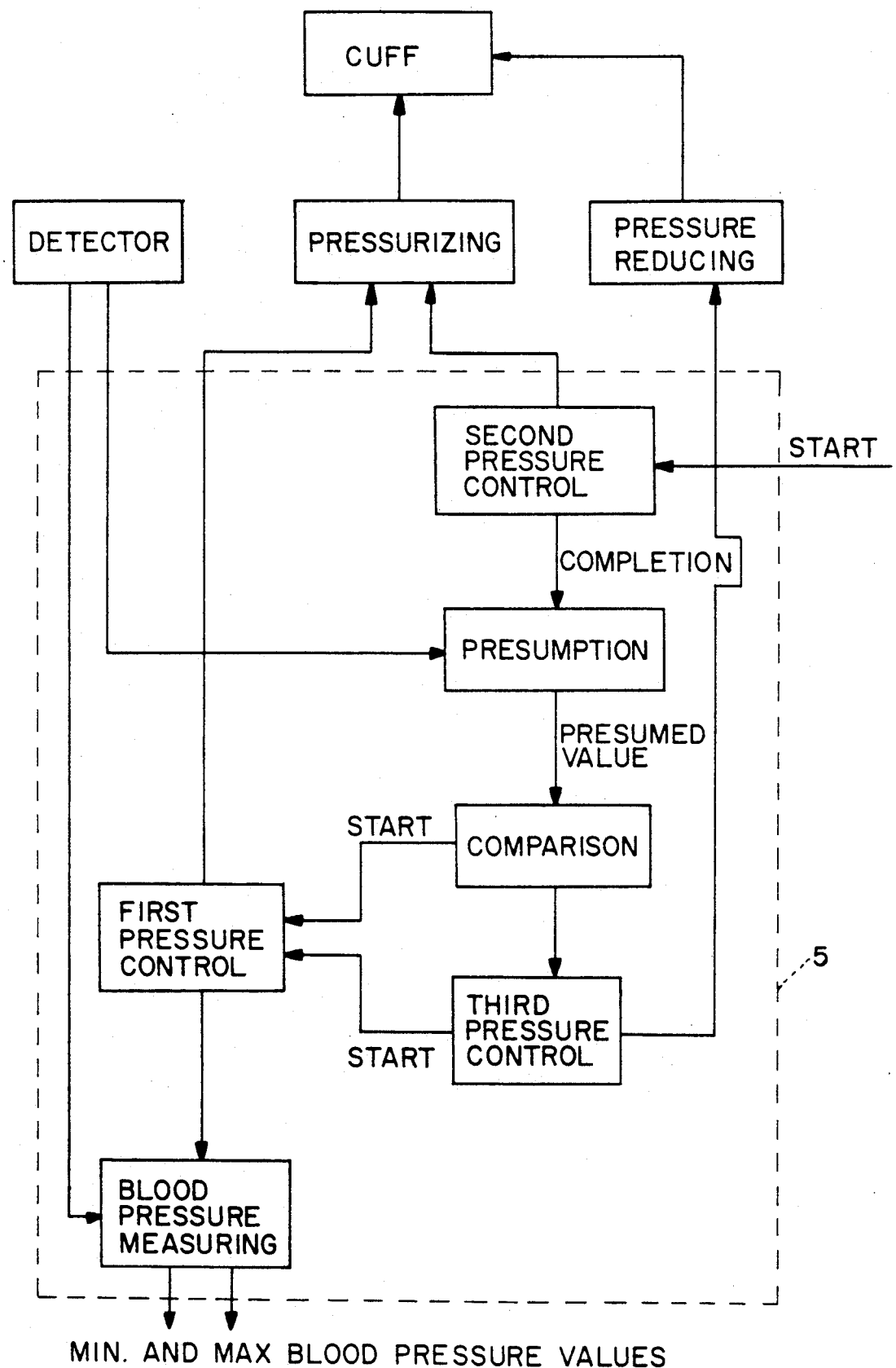
FIG. 1 is a block diagram illustrating schematically functions of an embodiment of the invention.
Figure 2:
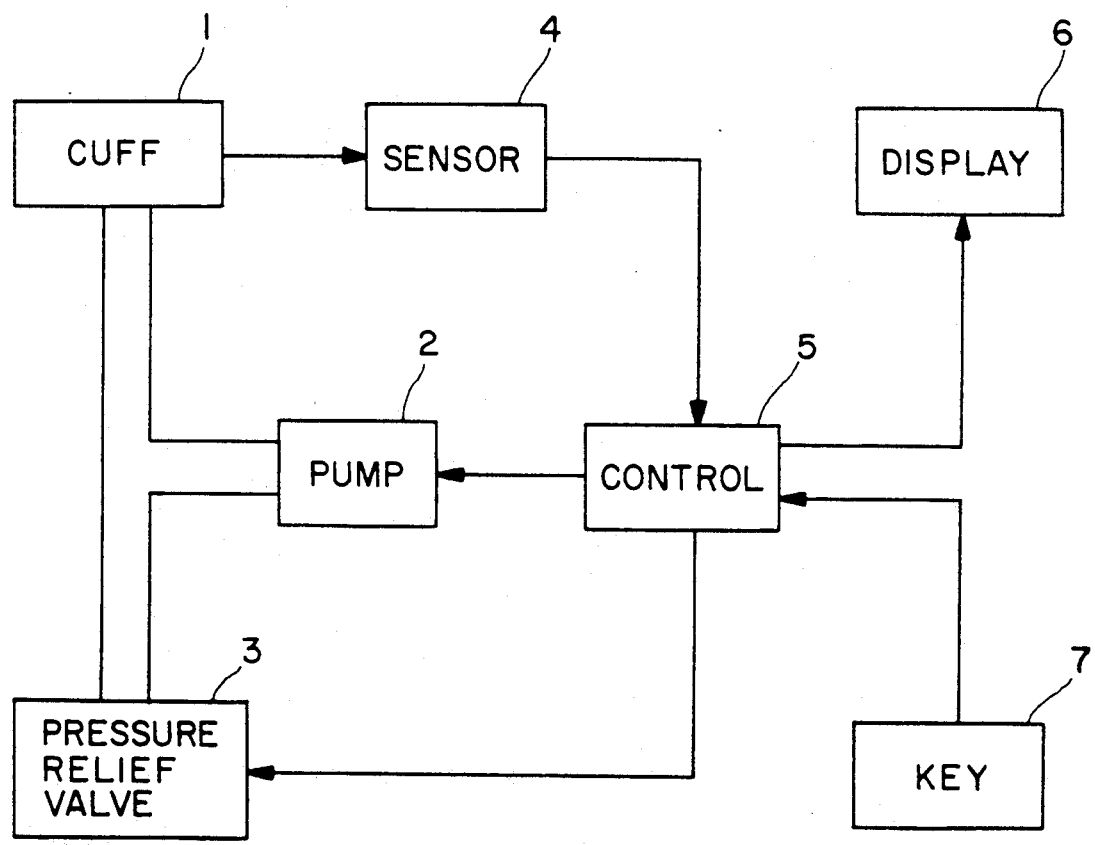
FIG. 2 is a block diagram of an apparatus of the invention.

FIG. 2 is a block diagram of an apparatus according to the invention. The apparatus of FIG. 2 comprises: a cuff 1 for compressing an artery of a body to be measured; a pressurizing pump 2 for increasing the pressure of the cuff 1; a pressure relief valve 3 for reducing the pressure of the cuff 1; a pulse pressure sensor 4 which detects pulse pressure vibrations (pulse wave) of an artery, the pulse pressure vibrations being transmitted to the cuff 1; a control unit 5 which controls the operations of the pump 2 and the pressure relief valve 3 and processes the values of the detected signals input from the pulse pressure sensor 4; a display device 6 for displaying blood pressure values, the maximum blood pressure values, etc.; and a key-input portion 7 having keys such as a start key through which a measurement start command is input. The control unit 5 is composed of a microcomputer.

Figure 3:
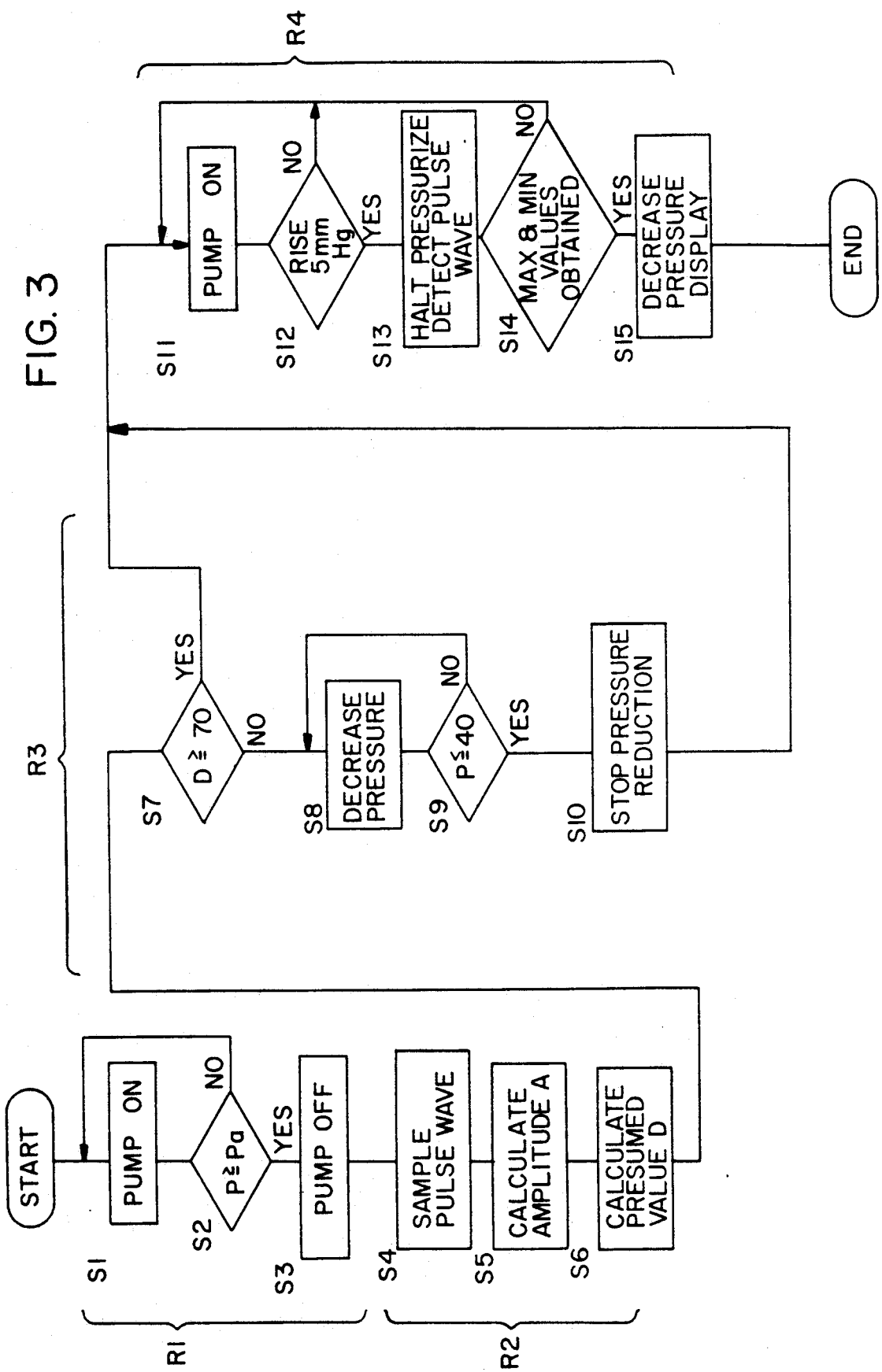
FIG. 3 is a flow chart of the apparatus of FIG. 2.

The operation of the apparatus of FIG. 2 will be described with reference to FIG. 3. Routine R1 consisting of steps S1 to S3 is an initial pressurizing routine. When the start key in the key-input portion 7 is depressed, the pump 2 is actuated to continuously pressurize the cuff 1 (step S1). The pressure P is compared in step S2 with a predetermined value Pa (in this case 60 mmHg) which is stored in a non-volatile memory in the control unit 5. The predetermined value Pa may be adjustable. When the pressure P reaches the predetermined value Pa, the continuous pressurization of the cuff 1 is ended (step S3), and routine R2 starts.

Figure 6:
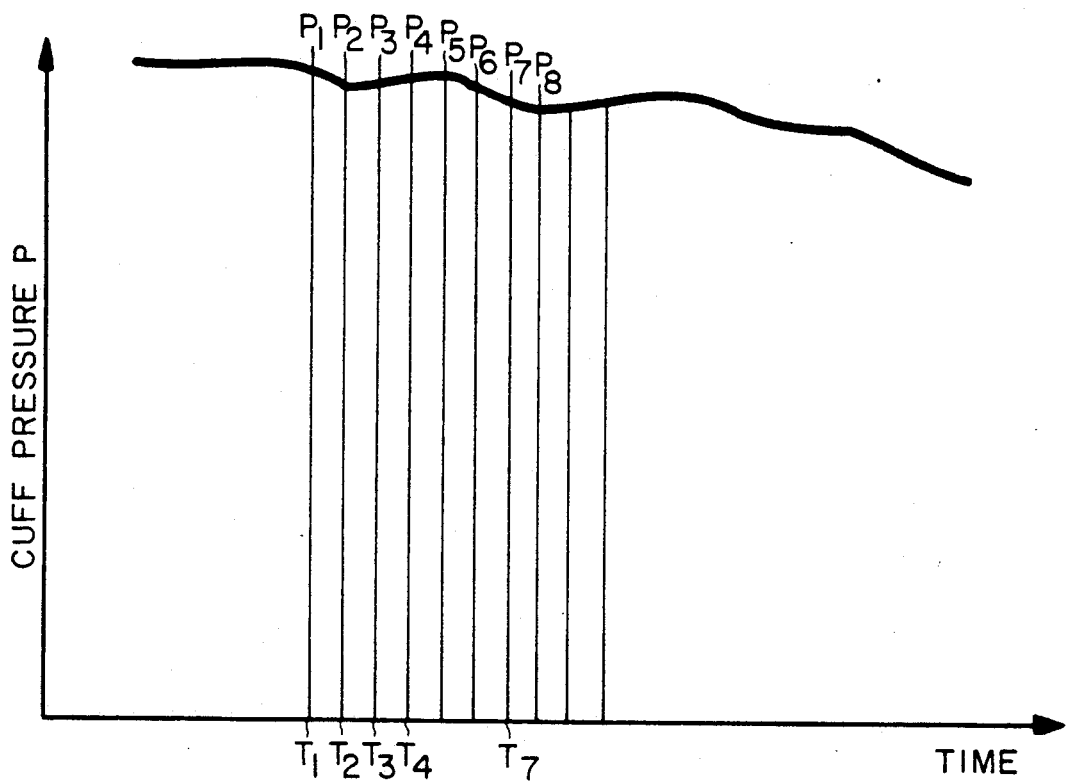
FIG. 6 is a graph for illustrating the presumption of the minimum blood pressure value.

In routine R2 consisting of step S4 to S6, a presumed value of the minimum blood pressure is obtained. The pulse wave detected by the sensor 4 is sampled to obtain an amplitude (peak-to-peak value) A of the pulse wave (step S4). FIG. 6 illustrates the pulse wave sampled at times $T_n$. The sampling interval $(T_n - T_{n-1})$ is set to 20 msecs. In this example, the pressure $P_2$ sampled at time $T_2$ is selected as a first minimum pressure value, the pressure $P_4$ sampled at time $T_4$ as a first maximum pressure value, and the pressure $P_7$ sampled at time $T_7$ is selected as a second minimum pressure value. The pulse wave amplitude A can be obtained by the following formula (1):

$$A = P_4 - \frac{P_2 - P_7}{T_7 - T_2}(T_4 - T_2) \quad (1)$$
$$\approx P_4 - \frac{P_2 - P_7}{2}$$

Figure 4:
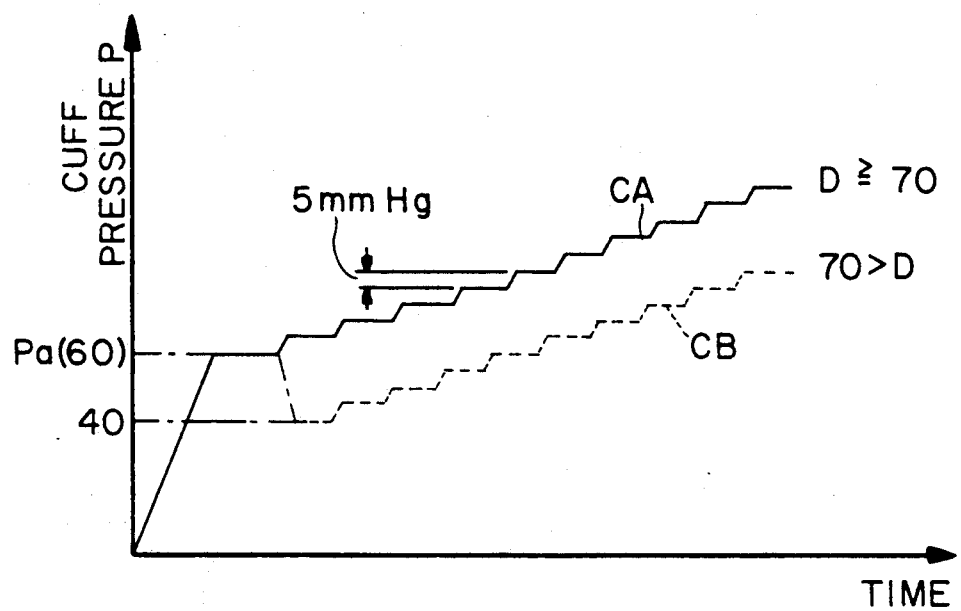
FIG. 4 is a graph showing the change of the pressure of a cuff used in the apparatus of FIG. 2.
Figure 5:
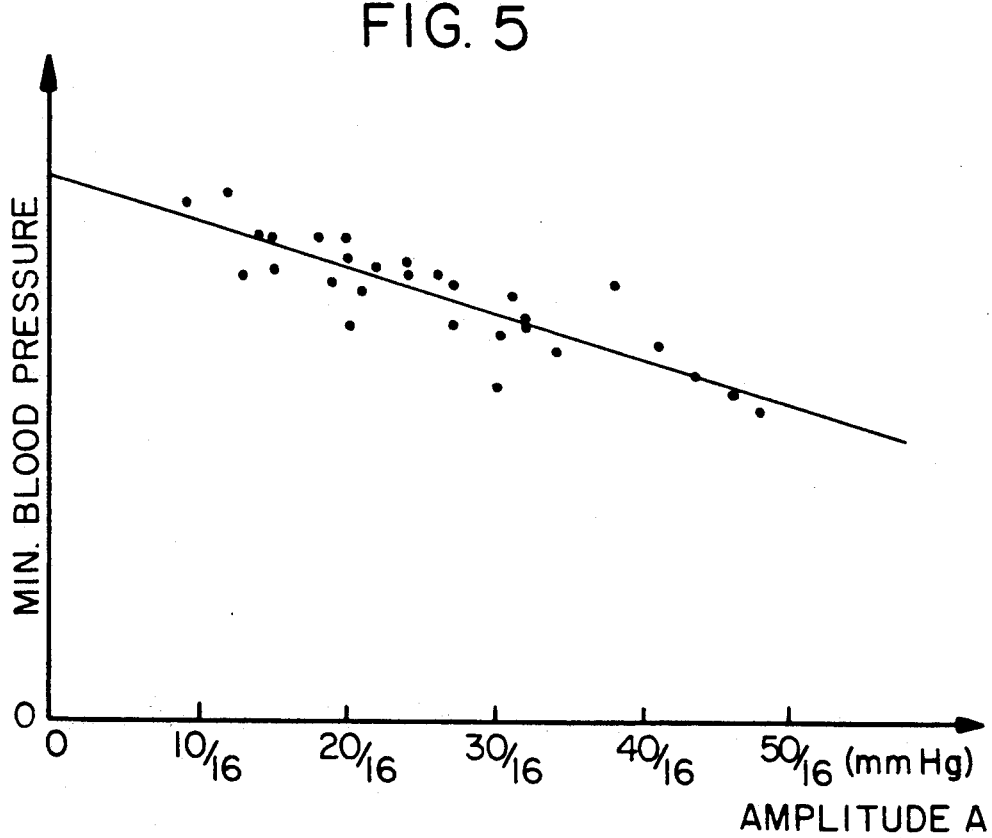
FIG. 5 shows the relation between pressures of a cuff and minimum blood pressure values.

From the pulse wave amplitude A thus obtained, the presumed value D of the minimum blood pressure is calculated. According to the researches conducted by the inventor, there is a relationship between pulse wave amplitudes A and minimum blood pressures as shown in FIG. 4, and the presumed value D can be obtained by the following formula:

$$D = -12.5A + 90 \quad (2)$$

In step S6, the minimum blood pressure is presumed using the formula (2).

In routine R3 consisting of steps S7 to S10, the starting pressure of the repressurization of the cuff 1 is determined in accordance with the level of the presumed value D. The presumed value D is compared with the first reference value Ea (70 mmHg) which is greater than the predetermined value Pa and by 10 mmHg and is stored in the memory of the control unit 5 (step S7). If the presumed value D is not less than the predetermined value Pa, the operation proceeds to step S11 (routine R4).

If the presumed value D is less than the first reference value Ea (70 mmHg), the operation proceeds to steps S8 and S9 in which the pressure relief valve 3 is actuated to reduce the pressure of the cuff 1 to a second reference value Eb (40 mmHg) which is smaller than the predetermined value Pa. When the pressure of the cuff 1 reaches the second reference value Eb, the reduction of the pressure of the cuff 1 is ceased (step S10), and the operation proceeds to step S11 to enter routine R4.

In step S11, the pump 2 is started again to increase the pressure of the cuff 1. When the pressure of the cuff 1 is increased by 5 mmHg, the pressurization is halted, and the pulse wave is detected to determine the maximum and minimum blood pressure values (steps S12 and S13). In step S14, the judgment whether the maximum and minimum blood pressure values have been obtained or not is conducted (step S14). Steps S11 to S14 are repeated until the maximum and minimum blood pressure values are obtained. FIG. 4 is a graph showing the change of the cuff pressure P. When the operation proceeds directly from step S7 to step S11 without executing steps S8 to S10, the cuff pressure P changes as shown by curve CA (solid line). In contrast, when the operation proceeds from step S7 to step S11 through steps S8 to S10, the cuff pressure P changes as shown by curve CB (broken line). The process in steps S11 to S14 may be similar to that described in the afore-mentioned U.S. patent application, and therefore its detailed description is omitted.

When the maximum and minimum blood pressure values are obtained, the pressure of the cuff 1 is reduced to a zero level, and the obtained maximum and minimum blood pressure values are displayed on the display device 6.

As described above, the control unit 5 functions as the second pressure control means in routine R1, as the pressure presumption means in routine R2, as the comparison means and third pressure control means in routine R3, and as the first pressure control means and blood pressure measuring means in routine R4.

Figure 7:
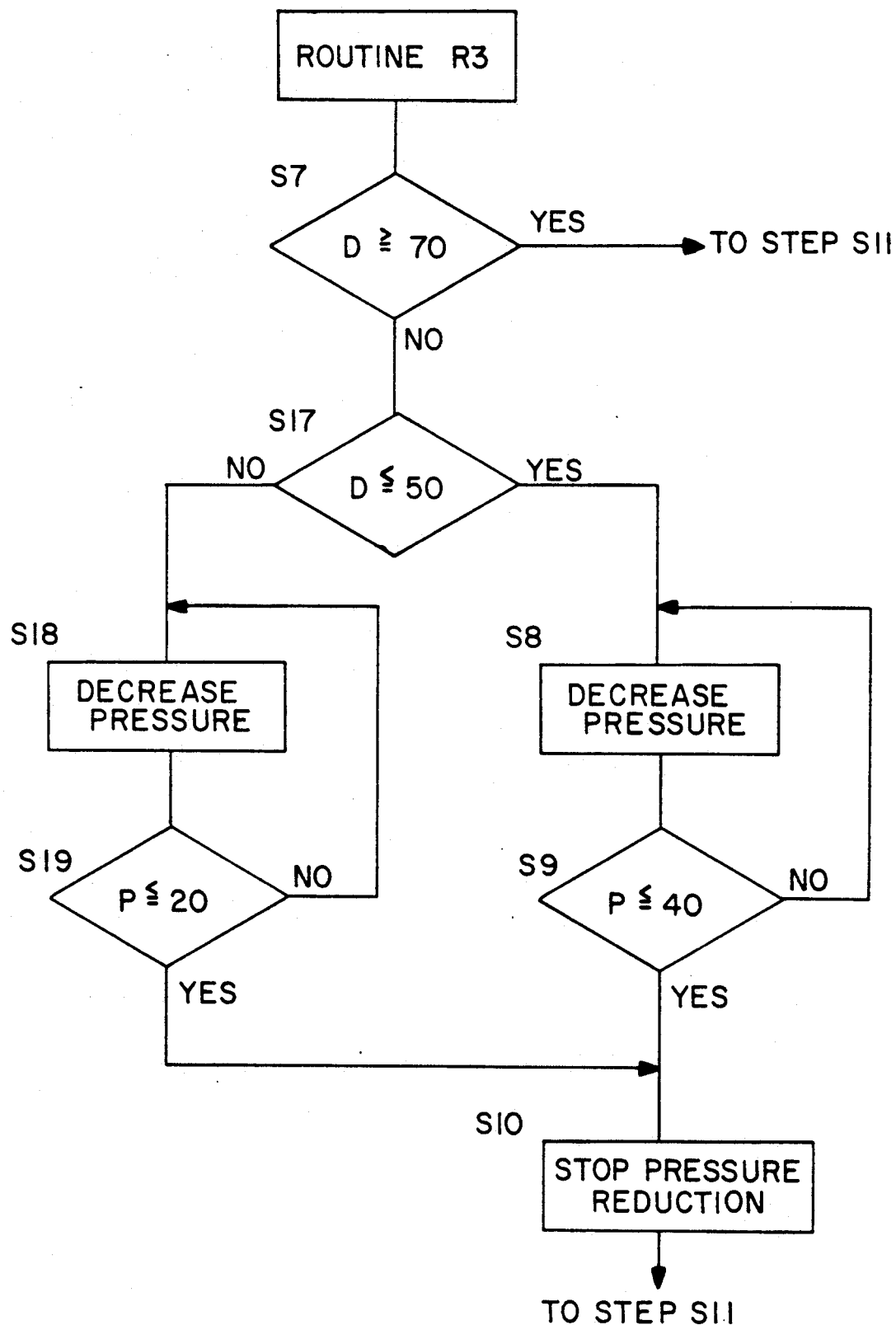
FIG. 7 is a flow chart of one routine in another apparatus of the invention.

FIG. 7 shows routine R3 in another apparatus of the invention. In the routine R3 in this apparatus, steps S17 to S19 are added so that the apparatus can be applied also to a subject the minimum blood pressure of which is very low. When the presumed value D is less than the predetermined value Pa (70 mmHg), the operation proceeds to step S17 in which the the presumed value D is compared with a third reference value Ec (50 mmHg) which is between the first and reference values Ea and Eb. When the presumed value D is greater than the third reference value Ec, the operation proceeds to step S8 to conduct the same process as that described above.

Figure 8:
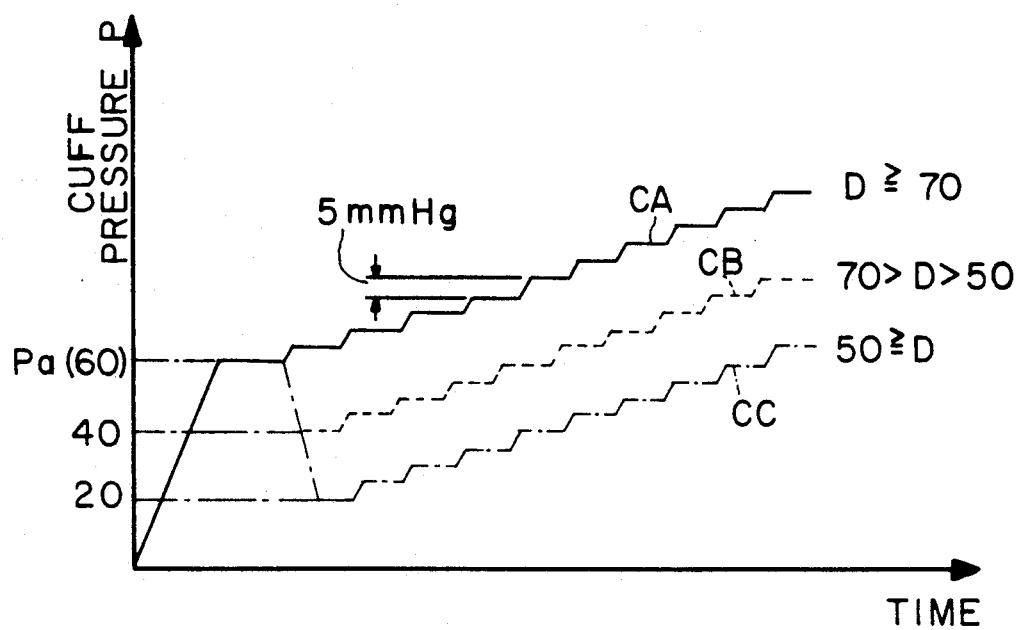
FIG. 8 is a graph showing the change of the pressure of a cuff used in the apparatus of FIG. 7.
Figure 9:
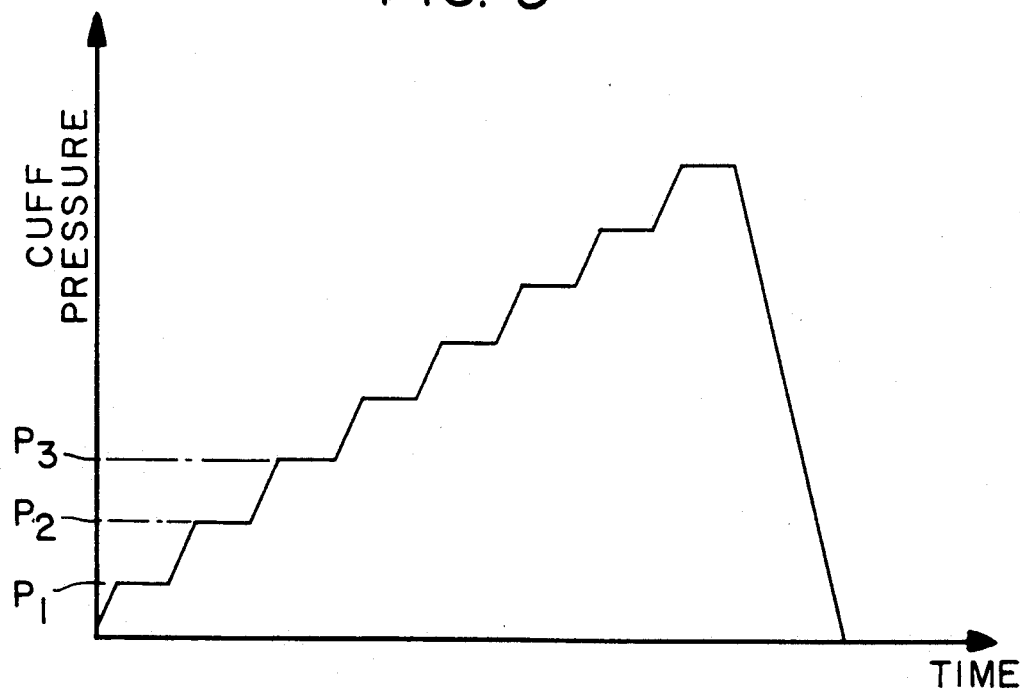
FIG. 9 is a graph showing the change of the pressure of a cuff used in a prior art apparatus.

When the presumed value D is less than the third reference value Ec, the pressure relief valve 3 is actuated to reduce the pressure of the cuff 1 to a fourth reference value Ed (20 mmHg) which is smaller than the second reference value Eb (step S18). When the pressure of the cuff 1 reaches the fourth reference value Ed (step S19), step S10 is executed to stop the reduction of the pressure of the cuff 1. FIG. 8 illustrates pressure changes in this apparatus. In FIG. 8, the chain line CC indicates the pressure change when steps S17 to S19 are executed.

Preferably, the reference values Ea to Ed, which are selected in due consideration of the predetermined value Pa so that the measurement of the maximum and minimum blood pressure are conducted in a short period of time, are stored in the memory of the control unit 5 when manufacturing the apparatus. It is also possible to modify the apparatus so that a user can adjust the reference values Ea to Ed.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. In an apparatus for automatically measuring blood pressure comprising: a cuff; a pressure means for applying a pressure to said cuff; a first pressure control means for controlling said pressure means to increase intermittently the pressure of said cuff; a detector means for detecting pressure pulses generated in said cuff; a pressure reducing means for reducing the pressure of said cuff; and a blood pressure measuring means for obtaining the minimum and maximum blood pressure values from pressure pulses which are detected during the stopping periods of the pressure increase, the improvement exists in that said apparatus further comprises:

a second pressure control means for controlling said pressure means to increase continuously the pressure of said cuff to a predetermined value;

a pressure presumption means for presuming the value of the minimum blood pressure from the amplitudes of pressure pulses detected by said detector after the completion of the continuous pressure increase;

a comparison means for comparing said presumption value with a first reference value which is greater than said predetermined value, said comparison means producing a signal to commence the operation of said first pressure control means when said presumed value is greater than said first reference value; and a third pressure control means for controlling said pressure reducing means to reduce the pressure of said cuff to a second reference value which is smaller than said first reference value, said third pressure control means producing a signal to commence the operation of said pressure control means when the pressure of said cuff has been reduced to said second reference value.

2. An apparatus according to claim 1, wherein said apparatus further comprises a further comparison means for comparing said presumed value with a third reference value which is between said first reference value and said second reference value, and a fourth pressure control means for controlling said pressure reducing means to reduce the pressure of said cuff to a fourth reference value which is smaller than said second reference value, said further comparison means producing a signal to commence the operation of said third pressure control means when said presumed value is greater than said third reference value, and said further comparison means producing a signal to commence the operation of said fourth pressure control means when said presumed value is smaller than said third reference value.

* * * * *